US00PP12558P2

(12) United States Plant Patent
Lemon et al.

(10) Patent No.: US PP12,558 P2
(45) Date of Patent: Apr. 23, 2002

(54) VARIETY OF GERANIUM NAMED 'GLOBAL PINK PEARL'

(75) Inventors: David Lemon, Lompoc, CA (US); Wendy Oglevee-O'Donovan, Scottsdale, AZ (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/469,995

(22) Filed: Dec. 22, 1999

(51) Int. Cl.[7] ..... A01H 5/00
(52) U.S. Cl. ..... Plt./332
(58) Field of Search ..... Plt./332

*Primary Examiner*—Bruce R. Campell
*Assistant Examiner*—A. Para
(74) *Attorney, Agent, or Firm*—Webb Ziesenheim Logsdon Orkin & Hanson, P.C.

(57) ABSTRACT

An ivy geranium plant with blooms colored fluorescent of electric pink to magenta with areas varying of degrees of lighter pink or lavender over medium green foliage.

1 Drawing Sheet

BACKGROUND OF THE INVENTION

This discovery relates to a new and distinct variety of *Pelargonium xpeltatum* identified by the varietal name of 'Global Pink Pearl' and Oglevee, Ltd. No. 8101. The new variety was discovered in a selective breeding program at Oglevee, Ltd. in Connellsville, Pa. The new variety is a selection from the crossing of 'Global Neon Cherry' (U.S. Plant Pat. No. 11,708) and the unpatented variety 'Peppermint Candy'. The bright cherry colored petals with opalescent stripes of the new variety are similar to those of 'Global Neon Cherry' and the cutting production, rooting speed, plant habit, and plant growth are similar to or better than 'Global Neon Cherry'. The new variety does not exhibit the longer trailing growth habit of 'Peppermint Candy' and has more stable petal striping. The new variety was first asexually reproduced on Jan. 21, 1999 in Connellsville, Pa. and has been found to retain its distinctive characteristics through successive generations. The plant was propagated asexually by cutting.

The new variety, when grown in a glass greenhouse in Connellsville, Pa. using full light, 60° F. night temperature and 68° F. day temperature and grown in a soilless media with constant fertilizer at 200–250 ppm nitrogen and potassium, has a response time of twelve weeks to flowering from a rooted cutting in a 10 inch pot. Three cuttings were planted per pot and pinched at four weeks after planting produce a finished hanging basket. The time to produce a root cutting is 24 to 28 days.

DESCRIPTION OF THE DRAWING

The accompanying photographic drawing illustrates the new variety 14 weeks from rooted cutting, with the color being as nearly true as is possible with color illustrations of this type.

DESCRIPTION OF THE PLANT

The following detailed descriptions set forth the characteristics of the new variety. The data which define these characteristics were collected from asexual reproductions carried out at Oglevee, Ltd., 152 Oglevee Lane, Connellsville, Pa. 15425. The color readings were taken under 200–220 footcandles of cool white fluorescent light on Aug. 3, 1999. Color references are to The R.H.S. Colour Chart of The Royal Horticultural Society of London and common color names.

THE PLANT

Classification:
- *Botanical.*—*Pelargonium xpeltatum.*
- *Varietal.*—Ivy geranium named 'Global Pink Pearl'.

Form: Cascading mound.
Height: 14–16 cm from media.
Growth: Cascading growth suitable for a hanging basket.
Strength: Stems are strong and do not break during handling.
Foliage: Stalked leaf attachment.
Leaves:
- *Size.*—6.6–7.7 cm across.
- *Shape.*—Reniform with cordate base.
- *Margin.*—Pedately lobed.
- *Texture.*—Slightly rough, pubescent.
- *Arrangement.*—Alternate, sometimes opposite.

Color:
- *Top.*—Green Group 137A.
- *Bottom.*—Yellow-Green Group 144A.
- *Zone.*—Insignificant zone present on only some leaves with the appearance of shadowy areas of Greyed-Purple Group 187A.

Ribs and veins:
- *Venation.*—Palmate.
- *Color.*—Yellow-Green Group 144A.

Petioles:
- *Length.*—5.7–7.5 cm.
- *Color.*—Yellow-Green Group 144A.
- *Texture.*—Pubescent.

Stem:
- *Color.*—Yellow-Green Group 144A.
- *Internode length.*—1.4–4.5 cm.
- *Texture.*—Pubescent.

THE BUD

Shape: Elongated elliptical cluster.
Size:
- *Bud.*—5.5–6.0 cm across when just showing color.
- *Umbel.*—1.3–1.5 cm long; 0.8–1.2 cm across when just showing color.

Sepals: A ring of 5 to 7 sepals is present; texture is pubescent; size is 3 to 5 mm wide and 1.4 to 1.6 cm long; color is Yellow-Green Group 144A.

INFLORESCENCE

Blooming habit: Continuous blooming; semi-double florets. Blooming period is 10 to 14 days and the duration of the bloom is 5 to 7 days.

Borne: Umbel, florets on pedicel, pedicel on peduncle.

Number of florets per umbel: 7–11.

Open florets:

*Size of fully open bloom.*—8.5–10.5 cm across.

*Form.*—Slightly ruffled; cupped.

*Color.*—Upper side of florets: Outer edge has an electric magenta/watermelon pink color of Red-Purple Groups 57A and 57B. Toward center there is a lighter area of blue-pink and pale lavender of Red-Purple Groups 63C, 68A, and 73A, and Purple Groups 75B and 75C which may also fade to white. These areas have streaks of bright pink in unpredictable patterns and amounts. The streaking colors include Red-Purple Groups 57A, 57B, 63B, 58B, and 58C. The base of the petals is lighter and may be pale pink or white. Underside of florets: Outer edge is Red-Purple Groups 57B and 57C, fading to a lighter Red-Purple Group 58B in some areas. The middle of the petal is white with streaking. Dark veining shows through from the varying shades and degrees of streaking. Eye: Present only on the top 2–4 petals as darker veining of Red-Purple Groups 59A or 61A and Red-Purple Group 61B. The eye occasionally includes two to three small spots with each spot including many small dots of Red-Purple Group 61A.

Petals:

*Number.*—9–10.

*Size.*—1.5–2.5 cm wide; 2.5–3.0 cm long.

Texture and appearance: Smooth, slightly reflective.

Tonality from a distance: Blooms with varying degrees of pink with a pearlescent appearance.

Petaloids:

*Quantity.*—0–4.

*Shape.*—Twisted, irregular. Some are petal-shaped with cut edges, some are filamentous and attached to anthers.

*Color.*—Same as petals.

Pedicel:

*Length.*—1.8–2.9 cm.

*Color.*—Yellow-Green Group 144A with some areas of Greyed-Purple Group 187C.

*Texture.*—Pubescent.

Peduncle:

*Length.*—9–15 cm.

*Color.*—Yellow-Green Group 144A.

*Texture.*—Pubescent.

Disease resistance: Not known.

Lasting quality: Very good post-harvest quality, new buds replace old buds quickly; less susceptible to oedema than other varieties in this market class.

Flower fragrance: None.

REPRODUCTIVE ORGANS

Stamens:

*Number.*—7 to 9.

*Anthers.*—2–3 mm long.

*Filaments.*—Length: 7–11 mm. Color: White Group 155A.

*Pollen.*—Orange-Red Group 34B.

Pistils:

*Number.*—1.

*Length.*—1.1–1.3 cm.

*Stigma color.*—Red Group 53B.

*Style.*—2–4 mm long.

*Ovaries.*—Yellow-Green Group 148D; pubescent; superior; 5–6 mm long.

Seed: Not produced.

GENERAL CHARACTERISTICS

The irregular and unpredictable amounts and shade of streaking makes this flower unique. The colors range from fluorescent/electric pink or magenta at outer edge to varying degrees of paler pinks including rather significant areas of blue-pink, almost lavender. Darker purple veining is present on some petals. The various shades of colors lends an almost pearlescent appearance to this flower. Finishing time and post-harvest quality are both very good when compared to the similarly colored variety 'Beauty of Eastborne'.

I claim:

1. A new and distinct variety of geranium plant named 'Global Pink Pearl' as described and illustrated herein.

* * * * *

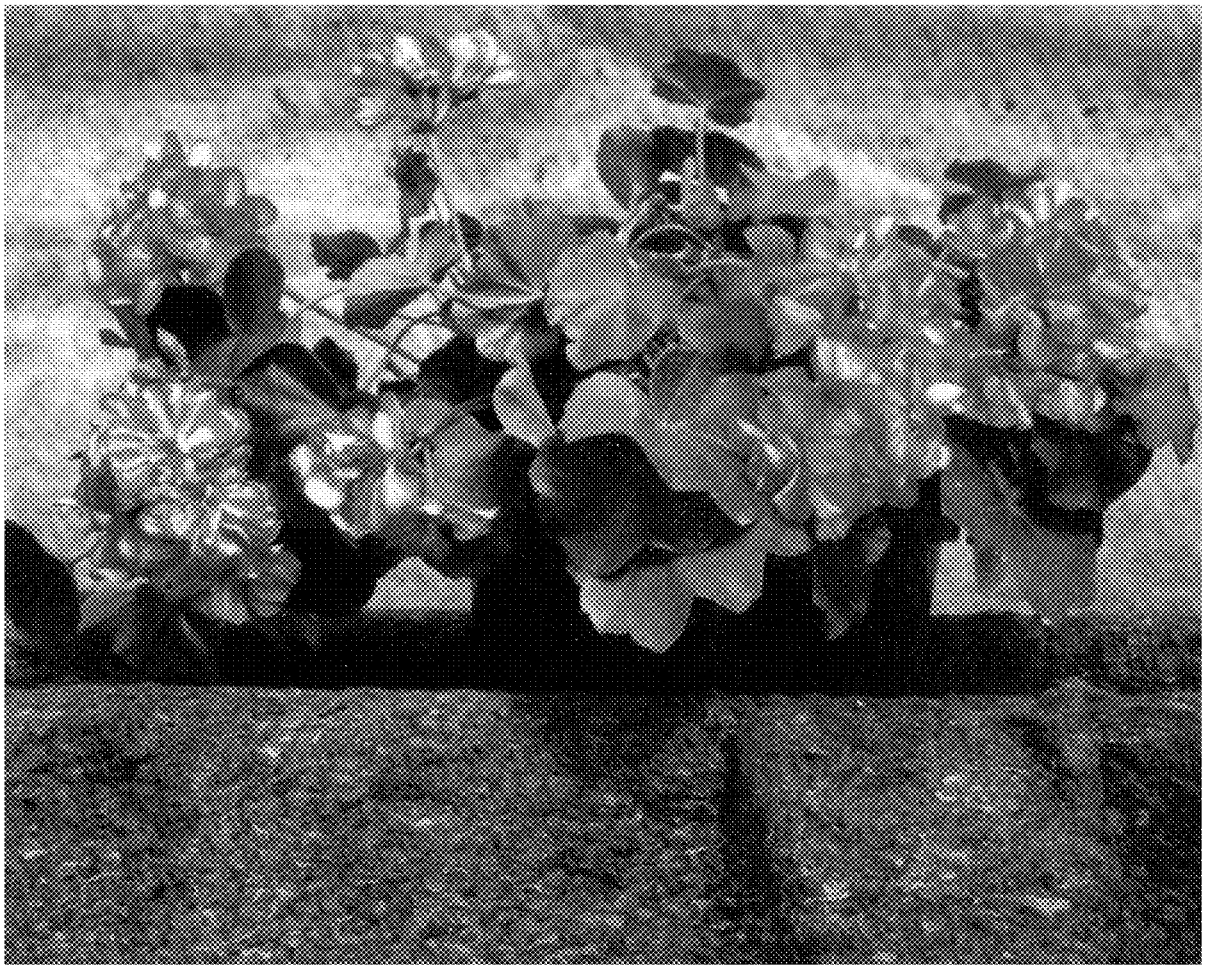

UNITED STATES PATENT AND TRADEMARK OFFICE

CERTIFICATE OF CORRECTION

PATENT NO. : PP 12,558 P2
DATED : April 23, 2002
INVENTOR(S) : David Lemon and Wendy Oglevee-O'Donovan It is certified that error appears in the above-identified patent and that said Letters Patent is hereby corrected as shown below:

Title page,
Item [75], Inventors, address of second inventor should read -- Scottdale, PA --

Signed and Sealed this

Twelfth Day of November, 2002

*Attest:*

*Attesting Officer*

JAMES E. ROGAN
*Director of the United States Patent and Trademark Office*